United States Patent
Walele et al.

(10) Patent No.: US 6,261,713 B1
(45) Date of Patent: Jul. 17, 2001

(54) DELIVERY SYSTEM FOR INORGANIC SUNSCREENS

(75) Inventors: Ismail I. Walele, Saddle Brook; Samad A. Syed, Paramus, both of NJ (US)

(73) Assignee: Finetex, Inc., Elmwood, NJ (US)

( * ) Notice: Subject to any disclaimer, the term of this patent is extended or adjusted under 35 U.S.C. 154(b) by 0 days.

(21) Appl. No.: 09/535,446

(22) Filed: Mar. 24, 2000

Related U.S. Application Data

(60) Provisional application No. 60/126,703, filed on Mar. 29, 1999.

(51) Int. Cl.$^7$ .............................................. A61K 7/42
(52) U.S. Cl. ................................. 429/54; 424/401
(58) Field of Search .................... 424/401, 59, 70.1, 424/70.9

(56) References Cited

U.S. PATENT DOCUMENTS 4,323,693  *  4/1982  Scala, Jr. ..................... 560/103
4,917,882  *  4/1990  Strobridge ..................... 424/59

* cited by examiner

Primary Examiner—Shelley A. Dodson
Assistant Examiner—Konata M. George
(74) Attorney, Agent, or Firm—Weingram & Associates, P.C.

(57) ABSTRACT

A novel delivery system for physical, inorganic sunscreens for use in sunscreen preparations is disclosed. One or more inorganic sunscreen agents, such as micronized zinc oxide and micronized titanium dioxide, is dispersed in a solid dispersion vehicle preferably selected from the group consisting of stearyl benzoate, behenyl benzoate and arachidyl benzoate, to thereby produce a solid dispersion of inorganic sunscreen agents for use in sun-screen preparations. The micronized sunscreens are embedded in a solid product which does not require mixing or regrinding before use. A solid formulation avoids the problems inherent in a fluid emulsion or dispersion, i.e., migration or settling out of the contents, which requires mixing and/or regrinding before use.

18 Claims, No Drawings

DELIVERY SYSTEM FOR INORGANIC SUNSCREENS

This application claims the benefit of 60/126,703 filed Mar. 29, 1999.

BACKGROUND OF THE INVENTION

1. Field of the Invention

The present invention relates to a novel delivery system for physical, i.e., inorganic, sunscreens, and the use of said delivery system in the preparation of stable sunscreen compositions.

2. Description of the Related Art

Sunscreen products may be emulsions, creams, lotions, gels, liquids, solid sticks, aerosols and all other forms of cosmetic compositions. Sunscreen compositions are applied topically to human skin to protect the skin against UV radiation damage. The term "sunscreen" herein is meant to include tanning lotions, sunscreens and sunblockers intended for topical application to human skin and/or hair to protect against ultraviolet radiation from the sun.

Active sunscreen ingredients which filter UV-A or UV-B rays harmful to the skin may be organic sunscreens such as PABAs (p-aminobenzoic acids), benzophenones, salicylate esters, and di-oxybenzone, octyl methoxycinnamate, and mixtures thereof, or physical sunscreens, which are inorganic compounds such as titanium dioxide and zinc oxide.

It has been found that inorganic sunscreen agents such as $TiO_2$ and zinc oxide are superior to customary organic sunscreen agents, as they are less irritating and offer better or broader UV protection. However, inorganic sunscreen agents are difficult to incorporate into sunscreen formulations. The invention relates to a novel delivery system for these inorganic sunscreen agents.

Micronized, also referred to as "microfine", physical sunscreens, such as zinc oxide and titanium dioxide, have a preferred particle size less than 1 micron. These particles of less than 1 micron or submicron size are effective sunblock agents. They do not scatter light, and therefore are useful in cosmetics, make-up, and sunscreen applications. Particles larger than 1 micron are undesirable as they inherently result in so-called "whitening effects".

The problem is that micronized $TiO_2$ and zinc oxide particles are susceptible to agglomeration after their production, during the post-manufacture period of transportation and handling. This tendency to agglomerate into clumps of much higher particle sizes (greater than 1 micron) reduces the efficacy of $TiO_2$ and Zinc Oxide as UV sunscreens and increases their white appearance on the skin. The ability of the micronized, inorganic sunscreens to function as UV-ray blocking agents is impeded if the micronized particle size is enlarged by agglomeration or dusting. Agglomeration also results in the deterioration of emulsions including such particles and negatively affects their stability and shelf-life during storage.

Not only are the fine, micronized inorganic sunscreen powders susceptible to agglomeration, but these particulates also have a tendency to show dusting effects during handling, such as charging to the mixing vessels.

The disadvantages of dusting and agglomeration, or re-agglomeration, are avoided by the novel delivery system of this invention.

Numerous references describe the use of micronized zinc oxide and titanium dioxide as sunscreen materials, in various formulations. None of these references, however, teach or suggest the specific novel delivery system of physical sunscreens of this invention, which prevents inorganic sunscreen pigment particles from accumulating to give agglomerates.

U.S. Pat. No. 4,323,693 to Scala, Jr. discloses a benzoic acid ester of isostearyl (C18) alcohol.

U.S. Pat. No. 4,917,882 to Stobridge discloses a gel-type sunscreen composition and a method of making same, comprising combining a sunscreen agent, polyethylene, and a benzoic ester, agitating and heating the mixture to a temperature and for a time sufficient to dissolve the polyethylene in the benzoate ester, and after the polyethylene is dissolved in the benzoate ester, cooling the mixture while agitating to produce a gelled sunscreen composition.

U.S. Pat. No. 5,340,567 to Cole et al. discloses a sunscreen composition comprising an extending medium such as a carrier or vehicle (such as mineral oil and polyethylene) and a synergistic combination of microfine titanium dioxide having a particle size of less than about 35 mu and zinc oxide having a particle size of less than about 50 mu. The particle sizes of the titanium oxide and zinc oxide are critical for obtaining a composition which is invisible on the skin.

U.S. Pat. No. 5,417,961 to Nearn et al. discloses a sunscreen composition comprising a water-in-oil emulsion which comprises an aqueous phase and an oil phase, the oil phase comprising polyethylene and an organic sunscreen agent. Microfine zinc oxide having a particle size in the range of from about 0.01 microns to about 0.25 microns is suspended in the oil phase.

U.S. Pat. No. 5,468,471 to Zecchino et al. discloses an organic dispersion of microfine titanium dioxide, of a particle size prior to agglomeration of about 10 nm to about 100 nm, and a cosmetically acceptable branched chained organic compound, preferably octyldodecyl neopentanoate, without any dispersing agent. The dispersion is prepared by subjecting the microfine titanium dioxide and the branched chain organic compound to a ball mill, roller mill or ultrasonic mixer, to grind the titanium dioxide in the organic compound and to disperse the titanium dioxide in the organic compound.

U.S. Pat. No. 5,476,643 to Fogel discloses use of two neopentyl glycol diesters as wetting, dispersing, spreading and detergent agents for micronized titanium dioxide and zinc oxide.

U.S. Pat. No. 5,498,406 to Nearn et al. discloses a sunscreen composition in oil-in-water emulsion form having about 0.5% to about 5% by weight of microfine titanium dioxide having a particle size of less than about 100 nm uniformly suspended therefrom, the composition further comprising a dispersing agent comprising a long chain saturated primary alcohol having an average of from about 25 to about 45 carbon atoms in the long chain, to stabilize the emulsion.

U.S. Pat. No. 5,543,136 to Aldous discloses making and using a water-in-oil emulsion comprising zinc oxide and an agent selected from the group consisting of tridecyl neopentanoate, $C_{12-15}$ alkyl benzoate, octyl neopentanoate and mixtures thereof in the emulsion's oil phase; titanium dioxide in the emulsion's water phase, a sunblocking agent, and oil phase emulsion components.

U.S. Pat. No. 5,605,652 to Tapley discloses a method of preparing sunscreens in which a dispersion of zinc oxide particles in an oil is formed by milling in the presence of a particulate grinding medium and mixed with cosmetically acceptable materials. A mixed oxide dispersion comprising an oil, particles of zinc oxide, particles of titanium oxide, and an organic dispersing agent is formed.

U.S. Pat. No. 5,573,753 to Tapley discloses a method of preparing sunscreen containing a zinc oxide dispersion comprising milling a particulate zinc oxide in an oil in the presence of a particulate grinding medium and an organic dispersing agent.

U.S. Pat. No. 5,599,529 to Cowie discloses an oil dispersion comprising an oil, titanium dioxide particles, and an organic dispersing agent for the particles. The dispersion has a solids content of greater than 40% by weight. The oil is selected from the class of oils consisting of fatty acid esters, fatty alcohols and saturated fatty acid di-esters. The oil dispersion is prepared by milling particulate titanium dioxide in an oil in the presence of a particulate grinding medium and an organic dispersing agent.

U.S. Pat. No. 5,725,844 to Gers-Berlag et al. discloses a sunscreen in the form of an oil in water emulsion or a hydro-dispersion, comprising one or more silanized hydrophobic inorganic pigments incorporated into the oily phase of the emulsions or hydrodispersions, one or more oil-soluble UV filter substances, one or more film-forming agents and optionally one or more water-soluble UV filter substances.

U.S. Pat. No. 5,730,993 to Allard et al. discloses a sunscreen comprising an ultrafine oil-in-water emulsion resulting from phase inversion of homogeneously and finely dispersed particulate of at least one nanopigment comprising a metal oxide, such as titanium dioxide or zinc oxide, having a particle size from 100 nm to 1,000 nm.

U.S. Pat. No. 5,747,012 to Dahms discloses a process for preparing a sunscreen comprising mixing a dispersion in an oil of particles of metallic oxide having an average particle size of less than 0.2 micrometers, with one or more emulsifiers, an aqueous phase, and a hydrophilic organic sunscreen, under conditions in which an emulsion is formed. The emulsion may be an oil-in-water emulsion or a water-in-oil emulsion. The dispersion of particles of metallic oxide is prepared by milling the particulate metallic oxide in the oil in the presence of a particulate grinding medium and in the presence of a dispersing agent.

U.S. Pat. No. 5,776,440 to Forestier et al. discloses a sunscreen composition comprising at least one coated nanopigment of metallic oxides, and at least one UV-screening fat-soluble polymer, in a cosmetically acceptable carrier.

U.S. Pat. No. 5,788,952 to Gers-Berlag et al. discloses a sunscreen comprising inorganic micropigments and optionally additional organic UV filter substances. The formulation is a hydrodispersion consisting of an inner lipid and an outer aqueous phase, free of emulsifiers, with the organic micropigments incorporated in the preferably liquid lipid phase of the hydrodispersion.

U.S. Pat. No. 5,817,298 to Galley et al. discloses a sunscreen composition comprising a water-in-oil emulsion which comprises 0.5 to 50% by weight of titanium dioxide particles having a mean particle size of less than 100 nm, each of the particles being substantially coated with phospholipid, together with a cosmetically acceptable carrier. Coating titanium dioxide particles with phospholipid reduces their tendency to clump.

The references describe various methods to prevent or reduce clumping of micronized physical (inorganic) sunscreens, so as to improve the efficacy of the sunscreen composition. However, among the foregoing patents, none disclose the specific delivery system for physical (inorganic) sunscreens of the invention or the use of such systems in the production of stable sunscreen compositions.

Thus, none of the references appear to teach or suggest a delivery system for physical (inorganic) sunscreens in which micronized sunscreens are embedded in a solid product which does not require mixing or regrinding before use. A solid formulation avoids the problems inherent in a fluid emulsion or dispersion, i.e., migration or settling out of the contents, which requires mixing and/or regrinding before use.

OBJECTS AND SUMMARY OF THE INVENTION

It is an object of the present invention to provide a novel delivery system for physical, inorganic sunscreens which results in non-agglomeration of the fine, micronized powders.

It is another object of the invention to provide a novel delivery system for physical, inorganic sunscreens for use in sunscreen applications.

It is yet another object of the invention to a novel delivery system for physical, inorganic sunscreens which results in non-dusting of the resulting fine, micronized powders.

It is a further object of the invention to provide a novel delivery system for physical, inorganic sunscreens which results in micronized powders which are easily re-meltable.

Yet another object of the invention is to provide a novel delivery system for physical, inorganic sunscreens which results in fine, micronized particles which are easily dispersible in the commonly used systems for sunscreen applications.

Further, it is an object of the invention to provide a method for dispersing micronized titanium dioxide and zinc oxide particles prior to utilization in cosmetic sunscreens.

Another object of the invention is to provide a novel delivery system for physical, inorganic sunscreens which results in micronized powders which are easily admixable in the oil phases of cosmetic creams, lotions, etc.

It is another object of the invention to provide a novel delivery system for physical, inorganic sunscreens which results in micronized powders which are easily grindable, if necessary.

Yet another object of the invention is to provide a novel delivery system for physical, inorganic sunscreens which results in more effective sunscreens.

It is another object of the invention to provide a novel delivery system for physical, inorganic sunscreens which results in sunscreens which are more effective over a longer period of time, reducing the need to reapply the sunscreen as frequently as would otherwise be necessary.

It is another object of the invention to provide a novel delivery system for physical, inorganic sunscreens which results in increased stability and shelf-life of the physical sunscreens and/or of the sunscreen preparations.

These and other objects are accomplished by providing an improved delivery system for micronized inorganic sunscreens in which micronized inorganic sunscreens are embedded in a solid product which does not require mixing or regrinding before use. A solid formulation avoids the problems inherent in a fluid emulsion or dispersion, i.e., migration or settling out of the contents, which requires mixing and/or regrinding before use. The micronized inorganic sunscreen is mixed into a pre-melted, solid vehicle such as Stearyl Benzoate (FINSOLV® 116 from Finetex, Inc., Elmwood Park, N.J.) and Behenyl Benzoate (FINSOLV® 137 from Finetex, Inc., Elmwood Park, N.J.), the mixture is mixed for intimate blending, and the solid dispersion discharged and cooled on flaking equipment or on any cooled surface.

The disadvantages of the known delivery systems for physical, inorganic sunscreens are overcome by the process of the present invention. The micronized physical sunscreens of the invention are non-agglomerating and non-dusting, and thus retain their effectiveness in sunscreen applications.

DETAILED DESCRIPTION OF THE INVENTION

This is accomplished by providing a novel delivery systems for physical, inorganic sunscreens. The micronized zinc oxide or titanium dioxide is mixed into a pre-melted, solid dispersion vehicle. The melting is done above the melting point of the respective vehicle. The mixture is subjected to mixing by means of a mixer for intimate blending. The mixture is then discharged and cooled on flaking equipment or on any cooled surface, especially cooled, flat, stainless steel belts. The product so cooled is a solid material, preferably in the form of flakes.

Titanium dioxide is an inorganic pigment widely used in paints, and in cosmetic products such as bar soaps, to enhance whiteness. The particle size of commonly used titanium dioxide is generally between 150 and 350 mu. Titanium dioxide also absorbs and scatters UV-radiation.

Zinc oxide is an inorganic substance which finds use as a white pigment in paints, papers and polymers, and as a physical sunblock by scattering and absorbing ultraviolet radiation.

Naturally, the grade of titanium dioxide and zinc oxide used as sunscreen agents in cosmetic preparations is different than that the grade used as a pigment in manufacturing paint, paper or plastics. The particles of inorganic sunscreen to be used in the present invention are fine, micronized particle size. If the particles are too large, over a micron, they are not effective as sunscreens. The particles may optionally be surface-treated with organic or inorganic coatings, such as aluminum stearate, or one or more oxides or hydrous oxides of aluminum, silicone, titanium, magnesium or zinc, etc., to prevent graying in sunlight.

Thus, inorganic sunscreens such as titanium dioxide or zinc oxide having a particle size less than 1 micron is used in the invention. Preferably, inorganic sunscreens having a particle size between 0.1 and 0.50 micron, and most preferably from about 10 nm to about 100 nm, are used.

Inorganic sunscreen agents such as titanium dioxide and zinc oxide have a tendency to agglomerate that reduces their efficacy, results in an unpleasant feel and gives a white appearance on the skin.

In general, the preferred method of producing the delivery system of the invention begins by melting the solid vehicle, and combining between about 10% and 60% of inorganic sunscreen agent and between about 40% and 90% of said melted vehicle, such as benzoate ester, depending upon the type of sunscreen preparation and its desired sunscreen efficacy or SPF. This mixture is then agitated and heated to a temperature and for a time sufficient to disperse the sunscreen agent in the vehicle. Any mixer or stirrer is suitable. Preferably, the temperature to which the mixture is heated will be above about 100° C. After the inorganic sunscreen is all dispersed in the vehicle, the mixture is cooled while agitating with a mixer or stirrer to thereby form a solid dispersion of the physical sunscreen. Preferably, the temperature to which the mixture is cooled while agitating is below about 60° C. The mixture is preferably homogenized by passing it through a homogenizer or other means, such as an in-line mill.

The solid dispersion vehicle is preferably Stearyl Benzoate (FINSOLV® 116 from Finetex Inc. of Elmwood Park, N.J., U.S. Pat. No. 4,323,694), Behenyl Benzoate (FINSOLV® 137 from Finetex Inc.), or Arachidyl Benzoate (a C-20 benzoate). Other dispersion vehicles which may be used in the process of the invention are solid fatty alcohols such as:

Cetyl Alcohol

Stearyl Alcohol

Cetearyl Alcohol

Behenyl Alcohol

Arachidyl Alcohol or

Higher Alcohols (C22+...)

The foregoing list is only exemplary of the type of esters on which the delivery system may be based, and, as such, is not to be considered limiting.

Additives which offer additional dispersing effects to the sunscreen compositions may be added in the vehicle delivery system at the time of melting of the dispersion vehicle. These are liquid emollients which may be added to the system in small quantities and do not affect the solid characteristics of the vehicle delivery system. Among them are:

$C_{12-15}$ Alkyl Benzoate (FINSOLV® TN from Finetex Inc., U.S. Pat. No. 4,323,694)

Octyl Dodecyl Benzoate (FINSOLV® BOD from Finetex Inc.)

PPG-15 Stearyl Ether Benzoate (FINSOLV® P from Finetex Inc., U.S. Pat. No. 4,791,097)

Dipropylene Glycol Dibenzoate (FINSOLV® PG-22 from Finetex Inc.)

The above and similar compounds are liquid emollients which promote the dispersion of the particulate inorganic sunscreen in the dispersion vehicle. Their addition is preferred but is not required. The quantity of the dispersing agent used depends on various factors but generally an amount from 1% to 20%, preferably from 1% to 10% by weight based on the weight of the particulate matter may be added.

These benzoate additives offer a processing benefit for the use of the solid vehicle delivery of micronized zinc oxide and titanium dioxide. Benzoate esters offer dispersing effects to the sunscreen compositions. The liquid benzoate esters identified above offer particularly effective dispersing effects and emolliency in the final compositions.

The micronized physical sunscreens of this invention in the solid dispersed form as prepared by the invention process may be incorporated into various cosmetic and personal care products such as hand and body creams, a suspension or dispersion in solvents or fatty substances, or alternatively, as lotions, ointments, oils, gels, emulsions such as a cream or a milk, solid sticks, facial cosmetics, lip balm products and the like, and may optionally be packaged as an aerosol or in the form of a foam or a spray.

The amount used in such compositions is dependent on the type of composition, the type and quantity of other ingredients, such as cosmetic ingredients used, and the amount and type of functional additives that are utilized. Typically, the percent concentration of the micronized zinc oxide or titanium dioxide used may very from 0.5% to 65%, by weight, depending upon the intended use of the particular sunscreen composition. For instance, low amounts are required in suntanning products which are not intended to prevent the sun's rays from reaching the skin. More substantial amounts are required for sunblocks products which are intended to prevent substantially all of the sun's rays from contacting the skin. A preferred, usable form carries about 60 parts of micronized zinc oxide or titanium dioxide per 40 parts of the benzoate ester or other dispersion vehicle.

The delivery system of the invention is advantageous as it results in micronized physical sunscreens which are:

non-dusting non-agglomerating easily re-meltable easily dispersible in the commonly used systems for sunscreen applications easily admixable in the oil phases of the cosmetic creams, lotions, etc.; and easily grindable, if necessary.

Another advantage is that the delivery system of the invention allows for pre-mixed, pre-dispersed sunscreen compositions suitable for long-term storage as stable, solid dispersions. Such compositions preferably comprise 10% to 60% by weight of inorganic sunscreen agents in a solid dispersion.

Another advantage is the solid dispersion has excellent homogeneity, i.e., the inorganic sunscreen pigments are very well dispersed in the solid dispersion, and when mixed into a sunscreen preparation for topical application.

Thus, the present invention provides novel stable and homogeneous sunscreen compositions comprising inorganic sunscreen pigments in a cosmetically acceptable vehicle of the solid dispersant type.

The delivery system of the invention makes the zinc oxide or titanium dioxide particles more dispersible, so that higher concentrations than were possible before may now be incorporated into stable fluid emulsions, dispersions, creams, lotions, ointments, etc. Thus, the delivery system of the invention enhances the dispersibility of the inorganic sunscreen particles, contributing to an improvement in the UV sunscreening efficiency and long-term stability of sunscreen compositions incorporating same.

Once the solid dispersion of zinc oxide or titanium dioxide in the dispersion vehicle, preferably a solid benzoate ester, has been prepared, it is ready for use in cosmetic sunscreen preparations as the active sunscreen ingredient.

In sum, the delivery system of the invention provides a means for delivering micronized inorganic sunscreens embedded in a Finsolv® benzoate ester product. There are currently no other solid dispersions of physical sunscreens on the market of the type of this invention. Liquid dispersions have drawbacks as the micronized sunscreen settles out over time, and must be stirred vigorously before use. In contrast, the invention contemplates a homogeneous, solid material into which the micronized physical sunscreen has been dispersed, which does not require mixing or regrinding prior to use.

The solid dispersions of physical sunscreens so prepared provide a convenient form of sunscreen which may be mixed with one or more cosmetically acceptable materials in the customary manner to formulate various types of sunscreen compositions. These may be used for cosmetic and/or dermatologic protection from the sun, and for the treatment, care and cleansing of the skin or hair, and as make-up. The formulation may take the form of anhydrous gel-type sunscreen compositions, oil in water emulsions and water in oil emulsions. There are no limitations on the use of the solid dispersions of the invention in sunscreen compositions. The cosmetic and dermatologic preparations are used by applying them to the skin and/or the hair in effective amounts in the customary manner.

Preferred compositions include emollients, selected from the group consisting of lanolin, isopropyl myristate, glyceryl stearate, cetyl alcohol, and dimethicone, and combinations thereof. The compositions may include further ingredients such as customarily used in such preparations, i.e., conventional adjuvants, including organic or inorganic sunscreens, fragrances, preservatives, bactericides, emulsifying agents, stabilizers, dispersants, anti-oxidants, thickeners, moisturizers, moisture-retaining agents, fats, oils, waxes, foam stabilizers, electrolytes, water-proofing agents, fillers, humectants, corrosion inhibitors, solubilizing agents, coloring pigments, vitamins, deodorizing agents, anti-perspirants, insect repellents, alkalinizing or acidifying agents, shaping agents, propellants, or any other ingredient generally used in the cosmetic field, as is known in the art.

Typically, in a general method for preparing a sunscreen lotion, hydroxyethyl cellulose (Natrosol® from Hercules, Inc. of Wilmington, Del.) is dispersed in water and heated to 75° C. to form a first Phase A. A second Phase B is prepared by separately heating glyceryl monostearate, DEA Oleth-3 phosphate, and cyclomethicone (345) to 75° C., and then adding Phase B to Phase A with mixing. Phase C, comprising the solid dispersion of inorganic sunscreen prepared as described above, is added in small portions with vigorous stirring by means of a mixer over a period of one hour. The mixture is cooled with stirring to 40° C. The loss of water is adjusted. When the temperature reaches 40° C., Phase D comprising propyleneglycol, diazolidinylurea, methyl paraben and propyl paraben (Germaben II from ISP, Wayne, N.J.) is added. The lotion is then homogenized with a hand homogenizer.

The ingredients and quantities used in any particular sunscreen composition will depend on the type of sunscreen, and the degree of SPF desired.

A further advantage of the delivery system of the invention is that lotions prepared thereby are invisible, i.e., do not have a whitening effect on the skin.

Another advantage is that sunscreen compositions made using the method of the invention have a pleasing appearance, because the benzoate ester provides a generally translucent medium. As a result, the composition can include dyes and the like to confer desirable colors to the composition.

Yet another advantage is that the compositions have been found to possess high substantivity, i.e., retention on the skin, even when reasonably immersed in water for 30 –60 minutes or more.

A further advantage of the invention is that the consistency, i.e., the viscosity and homogeneity, of the composition is stable over a wide range of temperatures. The preferred composition of the invention is generally stable at temperatures below 0° C. and above about 55° C. It will not liquify in high temperatures or freeze in low temperatures.

The delivery system of the invention provides a convenient and economical method for producing a wide variety of sunscreens.

The following are non-limiting examples of the novel delivery system for physical, inorganic, sunscreens, and the use of said delivery system in the preparation of stable sunscreen compositions. For ease of identification, each example is identified by both an Example Number and a Reference No., where applicable. Specifically, Example Nos. 1 through 11 are processes for pre-incorporation of physical sunscreens into benzoate esters according to the invention process. Example Nos. 12–14, 16, 18, 20, 22, and 24 are comparative examples showing processes for preparing sunscreen compositions using individual separate components, i.e., benzoate esters and physical sunscreens are added separately to make the lotions, as is known in the art. Examples Nos. 15, 17, 19, 21, 23, and 25 are examples of processes for preparing sunscreen lotions using the products of this invention which are blends of physical sunscreens and benzoate esters, as prepared in Example Nos. 1 through 11.

In the Examples, as well as throughout this application, the chemical and scientific symbols have their customary meanings and all percents are weight percents unless otherwise specified.

By "other process" in the Examples below, unless otherwise specified, is meant a process of the prior art as described, wherein benzoate esters and physical sunscreens are added separately to make the sunscreen lotions.

The following examples are intended to illustrate the scope of the present invention. As these examples are illustrative only, the invention should not be inferred to be limited to these examples.

TABLE I

| TRADE NAME/ PRODUCT | INCI NAME | SOURCE |
|---|---|---|
| FINSOLV ® TN* | C12–15 Alkyl Benzoate | Finetex ® Inc., |
| FINSOLV ® TPP** | C12–15 Alkyl Benzoate/ Dipropylene Glycol Dibenzoate/PPG-15 Stearyl Ether Benzoate | Finetex ® Inc., |
| FINSOLV ® 116 | Stearyl Benzoate | Finetex ® Inc., |
| FINSOLV ® 137 | Behenyl Benzoate | Finetex ® Inc., |
| NATROSOL | Hydroxyethyl Cellulose | Hercules, Inc., Wilmington, DE |
| Z-COTE | Zinc Oxide | Sun Smart, Inc., Wainscott, NY |
| Z-COTE HP1 | Zinc Oxide/dimethicone | Sun Smart, Inc., |
| T-COTE 031 | Titanium Dioxide/Dimethicone | Sun Smart, Inc., |
| UV TITAN (X-161) | Titanium Dioxide/Stearic Acid/Alumina | Presperse, Inc., Piscataway, NJ |
| UV TITAN (M-262) | Titanium Dioxide/ Dimethicone/Alumina | Presperse, Inc., |

*Patent Pending
**Patent No. 4,791,097

EXAMPLE #1 (121.84)

Dispersion of Titanium Dioxide (T-COTE 031 From Sunsmart, Inc., Wainscott, N.Y.) in FINSOLV® 137 & FINSOLV® TPP In 250 ml glass beaker equipped with thermometer, metallic stirrer added 22.5 grams FINSOLV® 137 and 10 parts (5.0 grams) FINSOLV® TPP. Heated the mixture to 60° C. to attain clear liquid on hot water bath. Started adding titanium dioxide powder (22.5 grams) in five equal portions over a period of two hours with good mixing and raising the temperature to 65° C. and maintaining the fluidity of the mixture all the time. Raised the temperature to 70° C. and held for one hour with good mixing with a stirrer. Cooled the mixture to 60° C. and discharged onto glass pyrex plate to obtain the flaked form.

Remarks:
1) Addition of titanium dioxide powder into liquid ester did not make any globules or clumps.
2) The mixture was in liquid form throughout the process.
3) Flakes were not too hard.
4) After discharge onto plate, there was no powder on the surface of the flakes.

EXAMPLE #2 (121-85)

Dispersion of Zinc Oxide (Z-COTE)in FINSOLV® 116

In 250 ml glass beaker equipped with thermometer, metallic stirrer added 25 grams FINSOLV® 116. Melted the flakes at 60° C. to attain clear liquid on hot water bath. Started adding zinc oxide powder (25 grams) in five equal portions over a period of two hours with good mixing and raising the temperature to 65° C. and maintaining the fluidity of the mixture all the time. Raised the temperature to 70° C. and held for one hour with good mixing. Cooled the mixture to 60° C. and discharged onto glass pyrex plate.

Remarks:
1) Addition of zinc oxide powder into liquid ester did not make any lumps, globules or agglomerates.
2) The mixture was liquid all the time during the addition of powder.
3) No separation was observed during addition of powder or during hold period.
4) Smooth incorporation of powder into liquid molten ester was observed.
5) Flakes containing powder were hard. No powder was found on the surface of the flakes.

EXAMPLE #3 (121-86)

Dispersion of Zinc Oxide (Z-COTE) in FINSOLV® 137

In 250 ml glass beaker equipped with thermometer, metallic stirrer added 25 grams FINSOLV® 137. Melted the flakes at 60° C. to attain clear liquid on hot water bath. Started adding zinc oxide powder (25 grams) in five equal portions over a period of two hours with good mixing and raising the temperature to 65° C. and maintaining the fluidity of the mixture all the time. Raised the temperature to 70° C. and held for one hour with good mixing. Cooled the mixture to 60° C. and discharged onto glass pyrex plate.

Remarks:
1) Addition of zinc oxide powder into liquid ester went very smoothly, no lumps or clumps.
2) The mixture was liquid all the time during the addition of powder and hold period.
3) Excellent incorporation of powder into liquid ester. No separation was observed with one uniform mixture.
4) Flakes containing powder were hard and brittle.
5) There was no powder on the surface of the flakes.

EXAMPLE #4 (121-87)

Dispersion of Zinc Oxide (Z-COTE) in FINSOLV® 137 & Behenyl Alcohol

In 250 ml glass beaker equipped with thermometer, metallic stirrer added 22.5 grams FINSOLV® 137 and 5.0 grams Behenyl Alcohol. Melted the flakes at 55° C. to attain clear liquid on hot water bath. Started adding zinc oxide powder (22.5 grams) in five equal portions over a period of two hours with good mixing and raising the temperature to 65° C. and maintaining the fluidity of the mixture all the time. Raised the temperature to 70° C. and held for one hour with good mixing. Cooled the mixture to 60° C. and discharged onto glass pyrex plate.

Remarks:
1) Addition of zinc oxide powder into liquid ester went very smoothly, no lumps or clumps.
2) The mixture was liquid and somewhat thinner compared to previous Example 3 during the addition of powder and hold period.
3) Smooth incorporation of powder into liquid ester. No separation was observed during the addition or hold period; one uniform mixture.
4) Flakes containing powder were hard.
5) There was no powder found on the surface of the flakes.

EXAMPLE #5 (121-88)

Dispersion of Zinc Oxide (Z-COTE) in FINSOLV® 116 & Cetyl Alcohol

In 250 ml glass beaker equipped with thermometer, metallic stirrer added 22.5 grams FINSOLV® 116 and 5.0 grams cetyl alcohol. Melted the flakes at 55° C. to attain clear liquid on hot water bath. Started adding zinc oxide powder (22.5 grams) in five equal portions over a period of two hours with good mixing and raising the temperature to 65° C. and maintaining the fluidity of the mixture all the time. Raised the temperature to 70° C. and held for one hour with good mixing. Cooled the mixture to 60° C. and discharged onto glass pyrex plate.

Remarks:
1) Addition of zinc oxide powder into liquid ester went very smoothly, no lumps or clumps.
2) The mixture was liquid and somewhat thinner compared to previous Example 2 during the addition of powder and hold period.
3) Smooth incorporation of powder into liquid ester. No separation was observed during the addition or hold period; one uniform mixture.
4) Flakes containing powder were hard.
5) There was no powder found on the surface of the flakes.

EXAMPLE #6 (121-89)

Dispersion of Zinc Oxide (Z-COTE) in FINSOLV® 137 & FINSOLV® TPP

In 250 ml glass beaker equipped with thermometer, metallic stirrer added 22.5 grams FINSOLV® 137 and 5.0 grams FINSOLV® TPP. Melted the flakes at 55° C. to attain clear liquid on hot water bath. Started adding zinc oxide powder (22.5 grams) in five equal portions over a period of two hours with good mixing and raising the temperature to 65° C. and maintaining the fluidity of the mixture all the time. Raised the temperature to 70° C. and held for one hour with good mixing. Cooled the mixture to 60° C. and discharged onto glass pyrex plate.

Remarks:
1) Addition of zinc oxide powder into liquid ester went very smoothly, no lumps or clumps.
2) The mixture was liquid and somewhat thinner compared to previous Example 3 during the addition of powder and hold period.
3) Smooth incorporation of powder into liquid ester. No separation was observed during the addition or hold period; one uniform mixture.
4) Flakes containing powder were hard.
5) There was no powder found on the surface of the flakes.

EXAMPLE #7 (121-90)

Dispersion of Zinc Oxide (Z-COTE HP1) in FINSOLV® 116

In 250 ml glass beaker equipped with thermometer, metallic stirrer added 25 grams FINSOLV® 116. Melted the flakes at 55° C. to attain clear liquid on hot water bath. Started adding zinc oxide powder (25 grams) in five equal portions over a period of two hours with good mixing and raising the temperature to 65° C. and maintaining the fluidity of the mixture all the time. Raised the temperature to 70° C. and held for one hour with good mixing. Cooled the mixture to 60° C. and discharged onto glass pyrex plate.

Remarks:
1) Addition of zinc oxide powder into liquid ester went very smoothly, no lumps or clumps.
2) The mixture was liquid during the addition of powder and hold period.
3) Smooth incorporation of powder into liquid ester. No separation was observed during the addition or hold period; one uniform, paste-like mixture.
4) Flakes containing powder were hard and slippery on the skin.
5) There was no powder found on the surface of the flakes.

EXAMPLE #8 (121-91)

Dispersion of Zinc Oxide (Z-COTE HP1) in FINSOLV® 137

In 250 ml glass beaker equipped with thermometer, metallic stirrer added 25 grams FINSOLV® 137. Melted the flakes at 55° C. to attain clear liquid on hot water bath. Started adding zinc oxide powder (25 grams) in five equal portions over a period of two hours with good mixing and raising the temperature to 65° C. and maintaining the fluidity of the mixture all the time. Raised the temperature to 70° C. and held for one hour with good mixing. Cooled the mixture to 60° C. and discharged onto glass pyrex plate.

Remarks:
1) Addition of zinc oxide powder into liquid ester went very smoothly, no lumps or clumps. Non-agglomerating and non-dusting addition process.
2) The mixture was liquid during the addition of powder and hold period.
3) Smooth incorporation of powder into liquid ester. No separation was observed during the addition or hold period; one uniform, paste-like mixture.
4) Flakes containing powder were hard, brittle and slippery on the skin.
5) There was no powder found on the surface of the flakes.

EXAMPLE #9 (121-195)

Dispersion of Titanium Dioxide (X-161) IN FINSOLV® 137

In 250 ml glass beaker equipped with thermometer, metallic stirrer added 50 grams FINSOLV® 137. Melted the flakes at 55° C. to attain clear liquid on hot water bath. Started adding titanium dioxide powder (50 grams) in five equal portions over a period of two hours with good mixing and raising the temperature to 65° C. and maintaining the fluidity of the mixture all the time. Raised the temperature to 70° C. and held for one hour with good mixing. Cooled the mixture to 60° C. and discharged onto glass pyrex plate.

Remarks:
1) Addition of titanium dioxide powder into liquid ester went very smoothly, no lumps or clumps. Non-agglomerating and non-dusting addition process.
2) The mixture was liquid during the addition of powder and hold period.
3) Smooth incorporation of powder into liquid ester. No separation was observed during the addition or hold period; one uniform, paste-like mixture.
4) Flakes containing powder were hard and brittle.
5) There was no powder found on the surface of the flakes.

EXAMPLE #10 (121-196)

Dispersion of Titanium Dioxide (X-161) IN FINSOLV® 116

In 250 ml glass beaker equipped with thermometer, metallic stirrer added 50 grams FINSOLV® 116. Melted the flakes at 55° C. to attain clear liquid on hot water bath. Started adding titanium dioxide powder (50 grams) in five equal portions over a period of two hours with good mixing and raising the temperature to 65° C. and maintaining the fluidity of the mixture all the time. Raised the temperature to 70° C. and held for one hour with good mixing. Cooled the mixture to 60° C. and discharged onto glass pyrex plate.

Remarks:
1) Addition of titanium dioxide powder into liquid ester went very smoothly, no lumps or clumps. Non-agglomerating and non-dusting addition process.
2) The mixture was liquid during the addition of powder and hold period.
3) Smooth incorporation of powder into liquid ester. No separation was observed during the addition or hold period; one uniform, thin paste-like mixture.
4) Flakes containing powder were hard and brittle and slippery on the skin.
5) There was no powder found on the surface of the flakes.

EXAMPLE #11 (121-197)

Dispersion of Titanium Dioxide (M262) IN FINSOLV® 137

In 250 ml glass beaker equipped with thermometer, metallic stirrer added 50 grams FINSOLV® 137. Melted the flakes at 55° C. to attain clear liquid on hot water bath. Started adding titanium dioxide powder (50 grams) in five equal portions over a period of two hours with good mixing and raising the temperature to 65° C. and maintaining the fluidity of the mixture all the time. Raised the temperature to 70° C. and held for one hour with good mixing. Cooled the mixture to 60° C. and discharged onto glass pyrex plate.

Remarks:
1) Addition of titanium dioxide powder into liquid ester went very smoothly, no lumps or clumps. Non-agglomerating and non-dusting addition process.
2) The mixture was liquid during the addition of powder and hold period.
3) Smooth incorporation of powder into liquid ester. No separation was observed during the addition or hold period; one uniform, paste-like mixture.
4) Flakes containing powder were hard and brittle, and slippery on the skin.
5) There was no powder found on the surface of the flakes.

Personal Care Product Formulations

To further demonstrate the superiority of the delivery system of the invention, a series of formulations was prepared as described in Example Nos. 12–25.

EXAMPLE #12 (121-106)

Moisturizing Sunscreen Lotion Formula Containing Zinc Oxide (Z-COTE)

| | INGREDIENTS (INCI) | % BY WT. |
|---|---|---|
| A. | Water | 72.75 |
| | Hydroxyethyl cellulose (NATROSOL ®) | 0.25 |
| B. | C12–15 Alkyl Benzoate (FINSOLV ® TN) | 8.00 |
| | Glyceryl Monostearate | 4.00 |
| | DEA Oleth-3 Phosphate | 3.00 |
| | Cyclomethicone (345) | 3.00 |
| C. | Zinc Oxide (Z-COTE) | 8.00 |
| D. | Propylene Glycol, Diazolidinylurea Methyl Paraben & Propyl Paraben (GERMABEN II) | 1.00 |
| | | 100.00 |

Procedure:
1. Disperse cellulose in water. Heat to 75° C.
2. Weigh (B) items. Heat to 75° C.
3. Add (B) to (A) with mixing.
4. Add (C) in small portions with vigorous stirring over a period of one hour
5. Cool to 40° C. Adjust loss of water.
6. At 40° C. add (D).
7. Homogenize the lotion with hand homogenizer.

EXAMPLE #13 (121-110)

Moisturizing Sunscreen Lotion Formula Containing Zinc Oxide (Z-COTE HP1)

| | INGREDIENTS (INCI) | % BY WT. |
|---|---|---|
| A. | Water | 72.75 |
| | Hydroxyethyl cellulose (NATROSOL ®) | 0.25 |
| B. | C12–15 Alkyl Benzoate (FINSOLV ® TN) | 8.00 |
| | Glyceryl Monostearate | 4.00 |
| | DEA Oleth-3 Phosphate | 3.00 |
| | Cyclomethicone (345) | 3.00 |
| C. | Zinc Oxide (Z-COTE HP1) | 8.00 |
| D. | Propylene Glycol, Diazolidinylurea Methyl Paraben & Propyl Paraben (GERMABEN II) | 1.00 |
| | | 100.00 |

Procedure:
1. Disperse cellulose in water. Heat to 75° C.
2. Weigh (B) items. Heat to 75° C.
3. Add (B) to (A) with mixing.
4. Add (C) in small portions with vigorous stirring over a period of one hour
5. Cool to 40° C. Adjust loss of water.
6. At 40° C. add (D).
7. Homogenize the lotion with hand homogenizer.

EXAMPLE #14 (121-114)

Moisturizing Sunscreen Lotion Formula Containing FINSOLV® 116 & Zinc oxide (Z-COTE) (Other Process)

| | INGREDIENTS (INCI) | % BY WT. |
|---|---|---|
| A. | Water | 72.75 |
| | Hydroxyethyl cellulose (NATROSOL ®) | 0.25 |
| B. | Stearyl Benzoate (FINSOLV ® 116) | 8.00 |
| | Glyceryl Monostearate | 4.00 |
| | DEA Oleth-3 Phosphate | 3.00 |
| | Cyclomethicone (345) | 3.00 |
| C. | Zinc oxide (Z-COTE) | 8.00 |
| D. | Propylene Glycol, Diazolidinylurea Methyl Paraben & Propyl Paraben (GERMABEN II) | 1.00 |
| | | 100.00 |

Procedure:
1. Disperse cellulose in water. Heat to 75° C.
2. Weigh (B) items. Heat to 75° C.
3. Add (B) to (A) with mixing.
4. Add (C) in small portions with vigorous stirring over a period of one hour
5. Cool to 40° C. Adjust loss of water.
6. At 40° C. add (D).
7. Homogenize the lotion with hand homogenizer.

EXAMPLE #15 (121-113)

Moisturizing Sunscren Lotion Formula Containing FINSOLV® 116 & Zinc Oxide (Z-COTE) (Invention Process)

| | INGREDIENTS (INCI) | % BY WT. |
|---|---|---|
| A. | Water | 72.75 |
| | Hydroxyethyl cellulose (NATROSOL ®) | 0.25 |
| B. | Glyceryl Monostearate | 4.00 |
| | DEA Oleth-3 Phosphate | 3.00 |
| | Cyclomethicone (345) | 3.00 |
| C. | Stearyl Benzoate/Zinc Oxide Flakes (Product of Ex. 2 (121–85) | 16.00 |
| D. | Propylene Glycol, Diazolidinylurea Methyl Paraben & Propyl Paraben (GERMABEN II) | 1.00 |
| | | 100.00 |

Procedure:

1. Disperse cellulose in water. Heat to 75° C.
2. Weigh (B) items. Heat to 75° C.
3. Add (B) to (A) with mixing.
4. Add (C) in small portions with vigorous stirring over a period of one hour
5. Cool to 40° C. Adjust loss of water.
6. At 40° C. add (D).
7. Homogenize the lotion with hand homogenizer.

EXAMPLE #16 (121-115)

Moisturizing Sunscreen Lotion Formula Containing FINSOLV® 137 & Zinc Oxide (Z-COTE) (Other Process)

| | INGREDIENTS (INCI) | % BY WT. |
|---|---|---|
| A. | Water | 72.75 |
| | Hydroxyethyl cellulose (NATROSOL ®) | 0.25 |
| B | Behenyl Benzoate (FINSOLV ® 137) | 8.00 |
| | Glyceryl Monostearate | 4.00 |
| | DEA Oleth-3 Phosphate | 3.00 |
| | Cyclomethicone (345) | 3.00 |
| C. | Zinc Oxide (Z-COTE) | 8.00 |
| D. | Propylene Glycol, Diazolidinylurea Methyl Paraben & Propyl Paraben (GERMABEN II) | 1.00 |
| | | 100.00 |

Procedure:

1. Disperse cellulose in water. Heat to 75° C.
2. Weigh (B) items. Heat to 75° C.
3. Add (B) to (A) with mixing.
4. Add (C) in small portions with vigorous stirring over a period of one hour
5. Cool to 40° C. Adjust loss of water.
6. At 40° C. add (D).
7. Homogenize the lotion with hand homogenizer.

EXAMPLE #17 (121-116)

Moisturizing Sunscreen Lotion Formula Containing FINSOLV® 137 & Zinc Oxide (Z-COTE) (Invention Process)

| | INGREDIENTS (INCI) | % BY WT. |
|---|---|---|
| A. | Water | 72.75 |
| | Hydroxyethyl cellulose (NATROSOL ®) | 0.25 |
| B. | Glyceryl Monostearate | 4.00 |
| | DEA Oleth-3 Phosphate | 3.00 |
| | Cyclomethicone (345) | 3.00 |
| C. | Behenyl Benzoate/Zinc Oxide Flakes (Product of Ex. 3 (121–86) | 16.00 |
| D. | Propylene Glycol, Diazolidinylurea Methyl Paraben & Propyl Paraben (GERMABEN II) | 1.00 |
| | | 100.00 |

Procedure:

1. Disperse cellulose in water. Heat to 75° C.
2. Weigh (B) items. Heat to 75° C.
3. Add (B) to (A) with mixing.
4. Add (C) in small portions with vigorous stirring over a period of one hour
5. Cool to 40° C. Adjust loss of water.
6. At 40° C. add (D).
7. Homogenize the lotion with hand homogenizer.

EXAMPLE #18 (121-117)

Moisturizing Sunscreen Lotion Formula Containing FINSOLV® 116 & Zinc Oxide (Z-COTE HP1) (Other Process)

| | INGREDIENTS (INCI) | % BY WT. |
|---|---|---|
| A. | Water | 72.75 |
| | Hydroxyethyl cellulose (NATROSOL ®) | 0.25 |
| B. | Stearyl Benzoate (FINSOLV ® 116) | 8.00 |
| | Glyceryl Monostearate | 4.00 |
| | DEA Oleth-3 Phosphate | 3.00 |
| | Cyclomethicone (345) | 3.00 |
| C. | Zinc Oxide (Z-COTE HP1) | 8.00 |
| D. | Propylene Glycol, Diazolidinylurea Methyl Paraben & Propyl Paraben (GERMABEN II) | 1.00 |
| | | 100.00 |

Procedure:

1. Disperse cellulose in water. Heat to 75° C.
2. Weigh (B) items. Heat to 75° C.
3. Add (B) to (A) with mixing.
4. Add (C) in small portions with vigorous stirring over a period of one hour
5. Cool to 40° C. Adjust loss of water.
6. At 40° C. add (D).
7. Homogenize the lotion with hand homogenizer.

EXAMPLE #19 (121-118)

Moisturizing Sunscreen Lotion Formula Containing FINSOLV® 116 & Zinc Oxide (Z-COTE HP1) (Invention Process)

| | INGREDIENTS (INCI) | % BY WT. |
|---|---|---|
| A. | Water | 72.75 |
|  | Hydroxyethyl cellulose (NATROSOL ®) | 0.25 |
| B. | Glyceryl Monostearate | 4.00 |
|  | DEA Oleth-3 Phosphate | 3.00 |
|  | Cyclomethicone (345) | 3.00 |
| C. | Stearyl Benzoate/Zinc Oxide Flakes (Product of Ex. 7 (121–90) | 16.00 |
| D. | Propylene Glycol, Diazolidinylurea Methyl Paraben & Propyl Paraben (GERMABEN II) | 1.00 |
| | | 100.00 |

Procedure:

1. Disperse cellulose in water. Heat to 75° C.
2. Weigh (B) items. Heat to 75° C.
3. Add (B) to (A) with mixing.
4. Add (C) in small portions with vigorous stirring over a period of one hour
5. Cool to 40° C. Adjust loss of water.
6. At 40° C. add (D).
7. Homogenize the lotion with hand homogenizer.

EXAMPLE #20 (121-194)

Moisturizing Sunscreen Lotion Formula Containing FINSOLV® 137 & Zinc Oxide (Z-COTE HP1) (Other Process)

| | INGREDIENTS (INCI) | % BY WT. |
|---|---|---|
| A. | Water | 72.75 |
|  | Hydroxyethyl cellulose (NATROSOL ®) | 0.25 |
| B. | Behenyl Benzoate (FINSOLV ® 137) | 8.00 |
|  | Glyceryl Monostearate | 4.00 |
|  | DEA Oleth-3 Phosphate | 3.00 |
|  | Cyclomethicone (345) | 3.00 |
| C. | Zinc Oxide (Z-COTE) (HP1) | 8.00 |
| D. | Propylene Glycol, Diazolidinylurea Methyl Paraben & Propyl Paraben (GERMABEN II) | 1.00 |
| | | 100.00 |

Procedure:

1. Disperse cellulose in water. Heat to 75° C.
2. Weigh (B) items. Heat to 75° C.
3. Add (B) to (A) with mixing.
4. Add (C) in small portions with vigorous stirring over a period of one hour
5. Cool to 40° C. Adjust loss of water.
6. At 40° C. add (D).
7. Homogenize the lotion with hand homogenizer.

EXAMPLE #21 (121-193)

Moisturizing Sunscreen Lotion Formula Containing FINSOLV® 137 & Zinc Oxide (Z-COTE HP1) (Invention Process)

| | INGREDIENTS (INCI) | % BY WT. |
|---|---|---|
| A. | Water | 72.75 |
|  | Hydroxyethyl cellulose (NATROSOL ®) | 0.25 |
| B. | Glyceryl Monostearate | 4.00 |
|  | DEA Oleth-3 Phosphate | 3.00 |
|  | Cyclomethicone (345) | 3.00 |
| C. | Behenyl Benzoate/Zinc Oxide Flakes (Product of EX. 8 (121–91) | 16.00 |
| D. | Propylene Glycol, Diazolidinylurea Methyl Paraben & Propyl Paraben (GERMABEN II) | 1.00 |
| | | 100.00 |

Procedure:

1. Disperse cellulose in water. Heat to 75° C.
2. Weigh (B) items. Heat to 75° C.
3. Add (B) to (A) with mixing.
4. Add (C) in small portions with vigorous stirring over a period of one hour
5. Cool to 40° C. Adjust loss of water.
6. At 40° C. add (D).
7. Homogenize the lotion with hand homogenizer.

EXAMPLE #22 (122-02)

Moisturizing Sunscreen Lotion Formula Containing FINSOLV® 116 & Titanium Dioxide (X-161) (Other Process)

| | INGREDIENTS (INCI) | % BY WT. |
|---|---|---|
| A. | Water | 72.75 |
|  | Hydroxyethyl cellulose (NATROSOL ®) | 0.25 |
| B. | Stearyl Benzoate (FINSOLV ® 116) | 8.00 |
|  | Glyceryl Monostearate | 4.00 |
|  | DEA Oleth-3 Phosphate | 3.00 |
|  | Cyclomethicone (345) | 3.00 |
| C. | Titanium Dioxide | 8.00 |
| D. | Propylene Glycol, Diazolidinylurea Methyl Paraben & Propyl Paraben (GERMABEN II) | 1.00 |
| | | 100.00 |

Procedure:

1. Disperse cellulose in water. Heat to 75° C.
2. Weigh (B) items. Heat to 75° C.
3. Add (B) to (A) with mixing.
4. Add (C) in small portions with vigorous stirring over a period of one hour
5. Cool to 40° C. Adjust loss of water.
6. At 40° C. add (D).
7. Homogenize the lotion with hand homogenizer.

EXAMPLE #23 (121-040)

Moisturizing Sunscreen Lotion Formula Containing
FINSOLV® 116 & Titanium Dioxide (X-161)
(Invention Process)

| | INGREDIENTS (INCI) | % BY WT. |
|---|---|---|
| A. | Water | 72.75 |
| | Hydroxyethyl cellulose (NATROSOL ®) | 0.25 |
| B. | Glyceryl Monostearate | 4.00 |
| | DEA Oleth-3 Phosphate | 3.00 |
| | Cyclomethicone (345) | 3.00 |
| C. | Stearyl Benzoate/Zinc Oxide Flakes (Product of Ex. 10 (121–196) | 16.00 |
| D. | Propylene Glycol, Diazolidinylurea Methyl Paraben & Propyl Paraben (GERMABEN II) | 1.00 |
| | | 100.00 |

Procedure:

1. Disperse cellulose in water. Heat to 75° C.
2. Weigh (B) items. Heat to 75° C.
3. Add (B) to (A) with mixing.
4. Add (C) in small portions with vigorous stirring over a period of one hour
5. Cool to 40° C. Adjust loss of water.
6. At 40° C. add (D).
7. Homogenize the lotion with hand homogenizer.

EXAMPLE #24 (122-01)

Moisturizing Sunscreen Lotion Formula Containing
FINSOLV® 137 & Titanium Dioxide (X-161)
(Other Process)

| | INGREDIENTS (INCI) | % BY WT. |
|---|---|---|
| A. | Water | 72.75 |
| | Hydroxyethyl cellulose (NATROSOL ®) | 0.25 |
| B. | Behenyl Benzoate (FINSOLV ® 137) | 8.00 |
| | Glyceryl Monostearate | 4.00 |
| | DEA Oleth-3 Phosphate | 3.00 |
| | Cyclomethicone (345) | 3.00 |
| C. | Titanium Dioxide (x-161) | 8.00 |
| D. | Propylene Glycol, Diazolidinylurea Methyl Paraben & Propyl Paraben (GERMABEN II) | 1.00 |
| | | 100.00 |

Procedure:

1. Disperse cellulose in water. Heat to 75° C.
2. Weigh (B) items. Heat to 75° C.
3. Add (B) to (A) with mixing.
4. Add (C) in small portions with vigorous stirring over a period of one hour
5. Cool to 40° C. Adjust loss of water.
6. At 40° C. add (D).
7. Homogenize the lotion with hand homogenizer.

EXAMPLE #25 (122-03)

Moisturizing Sunscreen Lotion Formula Containing
FINSOLV® 137 & Titanium Dioxide (X-161)
(Invention Process)

| | INGREDIENTS (INCI) | % BY WT. |
|---|---|---|
| A. | Water | 72.75 |
| | Hydroxyethyl cellulose (NATROSOL ®) | 0.25 |
| B. | Glyceryl Monostearate | 4.00 |
| | DEA Oleth-3 Phosphate | 3.00 |
| | Cyclomethicone (345) | 3.00 |
| C. | Behenyl Benzoate/Titanium Dioxide Flakes (Product of Ex. 9 (121–195) | 16.00 |
| D. | Propylene Glycol, Diazolidinylurea Methyl Paraben & Propyl Paraben (GERMABEN II) | 1.00 |
| | | 100.00 |

Procedure:

1. Disperse cellulose in water. Heat to 75° C.
2. Weigh (B) items. Heat to 75° C.
3. Add (B) to (A) with mixing.
4. Add (C) in small portions with vigorous stirring over a period of one hour
5. Cool to 40° C. Adjust loss of water.
6. At 40° C. add (D).
7. Homogenize the lotion with hand homogenizer.

Remarks on Examples of Invention Process
(Example Nos. 15, 17, 19, 21, 23, and 25)

The process of the invention comprises pre-incorporating physical sunscreens, e.g., titanium dioxide or zinc oxide, into the specified benzoate esters before dispersing into the combined phases A & B. Thus, a blend of physical sunscreen with benozate esters is pre-formed in the form of solid chunks or flakes and used to prepare sunscreen lotions. The following observations were made:

1. The addition of micronized zinc oxide powder or titanium dioxide powder pre-incorporated in stearyl and behenyl benzoates in solid form, preferably in the form of chunks or flakes, into combined portion of A & B was very, very easy. As each portion of the flakes melted in the combined portion A & B it became a part of the system. No dust or any kind of dusting problem whatsoever occurred. In particular, in Example Nos. 7 & 8, where dimethicone was present, it gives a smooth lotion at the end and helps during the process of making cosmetic lotions due to homogeneity and ease of dispersion.

2. In every Example using the invention process, there was not a single case of agglomeration. The process is non-agglomerating.

3. In each example of the use of the invention process (Example Nos. 15, 17, 19, 21, 23, and 25), a uniform lotion was obtained. As soon as the pre-incorporated blend in its solid flake or chunk form was added to the combined phase A & B, the sun-screen/ester blend went into the system without any difficulty as the individual portions of our invention product (Phase C) were being added progressively. There was no separation of any particles nor was there any stickiness on the sides of the vessel. The invention process-based blends give uniform lotions.

4. As soon as the chunks or flakes went into the combined mixture A & B, the chunks or flakes of the pre-blended products of this invention melted fast, and did not find any powder around or underneath the bottom of the mixer.

5. The incorporation of physical sunscreen powder in the form of solid chunks or flakes of FINSOLV® 116 and FINSOLV® 137 (stearyl & behenyl benzoates) into water and oil phase was very easy. As the flakes melted, it becomes part of the system with the sunscreen in it.

6. During homogenizing of the lotion with a hand homogenizer, did not feel the sound of the particles, i.e., grittiness of the particles. Before going through the homogenizer, the particles are well mixed and become part of the lotion.

7. After homogenizing, the spreadability of the lotion was excellent compared to the Examples using the other, known process. It was a very uniform lotion.

8. Lotions of Example Nos. 15, 17, 19, 21, 23, and 25) did not show whitening effect. No disruption of the particle distribution, i.e., there were no larger chunks in the lotion, it was all finely dispersed.

Remarks on Examples of Other, Prior Art Process
(Example Nos. 12–14, 16, 18, 20, 22, and 24)

The other, known process comprises adding physical sunscreens, i.e., titanium dioxide or zinc oxide, separately into the combined mixture of phases A & B. Benzoate esters and physical sunscreens are added separately to make the sunscreen lotions. The following observations were made:

1. Addition of micronized zinc oxide powder or titanium dioxide powder into combined portion of phases A & B was very difficult. Powder created lots of dust during addition. Even the presence of dimethicone in zinc oxide powder, and stearic acid and alumina in titanium dioxide, did not resolve the dusting problem.

2. In every Example of other process, i.e., Example Nos. 12–14, 16, 18, 20, 22, and 24, found formation of agglomeration of the particles.

3. In all cases, it was very difficult to make a uniform lotion. Powder tries to scatter in every direction with mixing. Decreasing the speed of the mixer created lumps around the mixer.

4. Water phase with physical sunscreen powder tries to stick around the mixer and beneath the mixer which creates a disproportionate amount of the sunscreen in the lotion.

5. Incorporation of physical sunscreen powder into oil and water phases was very cumbersome and tough.

6. When homogenizing the lotion with hand homogenizer, there was a distinct sound of the particles, i.e., grittiness of the particles, which was squeezing through the nozzle of the homogenizer.

7. After homogenizing, the spreadability of the lotion was very poor. The lotions were thick and non-uniform, i.e., heterogeneous.

8. Lotions showed whitening effect due to the uneven distribution of the particles in the system.

It will be understood that the embodiments described herein are merely exemplary and that a person skilled in the art may make many variations and modifications without departing from the spirit and scope of the invention. All such variations and modifications are intended to be included in the scope of the invention as described herein.

We claim:

1. A method of preparing a solid dispersion of physical inorganic sunscreens for use in sunscreen preparations comprising the steps of:
   a. melting a solid dispersion vehicle;
   b. adding one or more inorganic sunscreen agents to said melted dispersion vehicle;
   c. stirring and heating the mixture to a temperature and for a time sufficient to disperse said sunscreen agent in said dispersion vehicle;
   d. after the sunscreen agent is dispersed in said dispersion vehicle, cooling the mixture while stirring to thereby produce a solid dispersion of said one or more inorganic sunscreen agents for use in sunscreen preparations.

2. The method of claim 1 wherein said solid dispersion vehicle is selected from the group consisting of esters of benzoic acid and alcohols having from 16 to 22 carbons, and solid fatty alcohols selected from the group consisting of Cetyl Alcohol, Stearyl Alcohol, Cetearyl Alcohol, Behenyl Alcohol, Arachidyl Alcohol and higher alcohols having 22+ carbon atoms.

3. The method of claim 2 wherein said solid dispersion vehicle is preferably selected from the group consisting of stearyl benzoate, behenyl benzoate and arachidyl benzoate.

4. The method of claim 1 wherein said inorganic sunscreen agent is selected from the group consisting of micronized titanium dioxide and zinc oxide.

5. The method of claim 1 wherein the temperature to which the mixture is heated is above 60° C.

6. The method of claim 1 wherein between about 10% and 60% of one or more inorganic sunscreen agents is added to between about 40% and 90% of said melted dispersion vehicle.

7. The method of claim 1 wherein after step b., adding between 1 to 20% by weight based on the weight of the inorganic sunscreen of an emollient selected from the group consisting of $C_{12-15}$ Alkyl Benzoate (FINSOLV® TN from Finetex Inc.) Octyl Dodecyl Benzoate (FINSOLV® BOD from Finetex Inc.), PPG-15 Stearyl Ether Benzoate (FINSOLV® P from Finetex Inc.) and Dipropylene Glycol Dibenzoate (FINSOLV® PG-22 from Finetex Inc.).

8. The method of claim 1 wherein said solid dispersion while cooling is subjected to flaking.

9. The method of claim 1 further comprising, after step d., discharging said solid dispersion on a cooled surface.

10. A sunscreen preparation comprising a cosmetically acceptable carrier and an effective amount of a solid dispersion of said one or more inorganic sunscreen agents according to claim 1 as the active sunscreen ingredient.

11. The sunscreen preparation of claim 10 wherein said solid dispersion is from about 5% to about 50% by weight of said sunscreen preparation.

12. A method of protecting human skin or hair from ultraviolet radiation comprising applying to the skin or hair an effective quantity of a sunscreen preparation according to claim 10.

13. A homogeneous, storage-stable, solid dispersion of micronized inorganic sunscreen comprising a solid dispersion vehicle selected from the group consisting of stearyl benzoate, behenyl benzoate and arachidyl benzoate, and one or more inorganic sunscreen agents selected from the group consisting of micronized titanium dioxide and zinc oxide.

14. The solid dispersion of claim 13 comprising between about 40% and 90% of said solid dispersion vehicle and between about 10% and 60% of said one or more inorganic sunscreen agents.

15. The solid dispersion of claim 13 preferably comprising 50% of said solid dispersion vehicle and 50% of said one or more inorganic sunscreen agents.

16. A homogeneous, storage-stable, solid dispersion of one or more inorganic sunscreen agents selected from the group consisting of micronized titanium dioxide and micronized zinc oxide and a solid dispersion vehicle selected from the group consisting of stearyl benzoate, behenyl benzoate and arachidyl benzoate, wherein said solid dispersion is prepared by melting said solid dispersion vehicle, adding said one or more inorganic sunscreen agents, stirring and heating the mixture to a temperature and for a time sufficient to disperse said sunscreen agent in said dispersion vehicle, and after said sunscreen agent is dispersed in said dispersion vehicle, cooling said mixture while stirring to thereby produce a solid dispersion of inorganic sunscreen, and discharging said solid dispersion on a cooled surface.

17. The solid dispersion of claim 16 comprising between about 10% and 60% of one or more of said inorganic sunscreen agents blended into between about 40% and 90% of said dispersion vehicle.

18. A sunscreen preparation comprising a cosmetically acceptable carrier and from about 5% to about 50% of the solid dispersion of one or more inorganic sunscreen agents of claim 16.

* * * * *